United States Patent
Samant et al.

(10) Patent No.: US 12,336,972 B2
(45) Date of Patent: Jun. 24, 2025

(54) SYNERGISTIC NUTRITIONAL COMPOSITIONS FOR TREATING NEUROCOGNITIVE DISORDERS

(71) Applicant: CELAGENEX RESEARCH (INDIA) PVT. LTD., Maharashtra (IN)

(72) Inventors: Rajaram Samant, Thane West (IN); Rajendra Prasad Tongra, Jaipur (IN)

(73) Assignee: CELAGENEX RESEARCH (INDIA) PVT. LTD., Thane (IN)

( * ) Notice: Subject to any disclaimer, the term of this patent is extended or adjusted under 35 U.S.C. 154(b) by 0 days.

(21) Appl. No.: 17/571,105

(22) Filed: Jan. 7, 2022

(65) Prior Publication Data

US 2022/0233484 A1    Jul. 28, 2022

(30) Foreign Application Priority Data

Jan. 22, 2021 (IN) .............................. 202021046067

(51) Int. Cl.
| | | |
|---|---|---|
| *A61K 31/198* | (2006.01) | |
| *A61K 9/00* | (2006.01) | |
| *A61K 31/185* | (2006.01) | |
| *A61P 25/28* | (2006.01) | |

(52) U.S. Cl.
CPC .......... *A61K 31/198* (2013.01); *A61K 9/0053* (2013.01); *A61K 31/185* (2013.01); *A61P 25/28* (2018.01)

(58) Field of Classification Search
CPC .............................. A61P 25/28; A61K 9/0053
See application file for complete search history.

(56) References Cited

U.S. PATENT DOCUMENTS

| | | | |
|---|---|---|---|
| 9,616,038 B2 | 4/2017 | Liu et al. | |
| 2006/0251714 A1* | 11/2006 | Laurin | A61K 9/5047 424/464 |
| 2020/0121624 A1* | 4/2020 | Liu | A61K 33/06 |

FOREIGN PATENT DOCUMENTS

| | | |
|---|---|---|
| EP | 3219306 A1 | 9/2017 |
| WO | 2010/096925 A1 | 9/2010 |

* cited by examiner

*Primary Examiner* — Jeffrey S Lundgren
*Assistant Examiner* — Eric Tran
(74) *Attorney, Agent, or Firm* — Maschoff Brennan (57) ABSTRACT

The invention disclosed herein is related to novel synergistic nutritional compositions for treating neurocognitive disorders. Particularly, the invention provides a stable nutritional composition for treating neurocognitive disorders comprising an exogenous blend of magnesium L-threonate and homotaurine present in the weight ratio of 1:0.1 to 1:1, along with pharmaceutically acceptable excipients. Further, the present synergistic nutritional composition is useful for treating neurocognitive disorders such as Alzheimer's disease (AD), dementia, and Attention-deficit/hyperactivity disorder.

4 Claims, 5 Drawing Sheets

SYNERGISTIC NUTRITIONAL COMPOSITIONS FOR TREATING NEUROCOGNITIVE DISORDERS

FIELD OF THE INVENTION

The present invention relates to novel synergistic nutritional compositions for treating neurocognitive disorders. Particularly, the invention provides synergistic composition of nutrients for improving cognitive function in a subject in need thereof.

More particularly, the invention relates to nutritional compositions comprising synergistic combination of magnesium salt of sugar acid and sulfur-containing amino acid along with pharmaceutically acceptable excipients; wherein the magnesium salt of sugar acid is L-Threonic acid magnesium salt (L-TAMS); and sulfur-containing amino acid is homotaurine (HT) which are present in a specific weight ratio.

Further, the present synergistic nutritional composition is useful for treating neurocognitive disorders such as Alzheimer's disease; early-stage adult dementia; early Alzheimer's disease; prodromal Alzheimer's disease; adult attention deficit hyperactive disorder (ADHD); anxiety/sleep depression; Parkinson's disease; mild cognitive impairment (MCI); Alzheimer's amyotrophic lateral sclerosis (ALS); epilepsy; traumatic brain injury; and dementia.

BACKGROUND OF THE INVENTION

Neurocognitive disorders (NCDs) typically include delirium, and mild and major neurocognitive disorder previously known as dementia.

The Diagnostic and Statistical Manual of Mental Disorders, 5th Edition [DSM-5] defines six key domains of cognitive function namely executive function, learning and memory, perceptual-motor function, language, complex attention, and social cognition.

Neurocognitive disorders are diagnosed as mild and major based on the severity of their symptoms. While anxiety disorders, mood disorders, and psychotic disorders can also have an effect on cognitive and memory functions, the Diagnostic and Statistical Manual of Mental Disorders, fourth edition, text revision (DSM-IV-TR) does not consider these as cognitive disorders, because loss of cognitive function is not the primary (causal) symptom. Additionally, developmental disorders such as autism spectrum disorder are typically developed at birth or early in life as opposed to the acquired nature of neurocognitive disorders.

NCDs also known as cognitive disorders or dementias are those that involve impairment in cognitive abilities such as memory, problem solving, and perception. NCDs commonly result from Alzheimer's or Parkinson's disease. Cognitive dysfunction is a broad term for a variety of issues occurring in the elderly. From mild cognitive impairment (MCI) to dementia, there are several degrees and levels of cognitive dysfunction.

Alzheimer's disease (AD) accounts for 60% to 70% of cases of neurocognitive disorders. Alzheimer's is a chronic neurodegenerative disease that usually starts slow and worsens over time.

Alzheimer's disease is the most serious and common form of dementia. It is a progressive disease with symptoms developing gradually before they intensify over time. In its late stages, the disease can make it difficult for a person to handle daily tasks, think clearly, control bodily movements and live independently. Alzheimer's disease accounts for 60-80% of dementia cases and is the sixth leading cause of death in the United States.

Although Alzheimer's disease accounts for majority of the cases of neurocognitive disorders, there are various medical conditions that affect mental functions such as memory, thinking, and the ability to reason, including frontotemporal degeneration, Huntington's disease, Lewy body disease, traumatic brain injury (TBI), Parkinson's disease, prion disease, and dementia/neurocognitive issues due to human immunodeficiency virus (HIV) infection.

Ageing has long been associated with a gradual decline in memory, cognition and thinking abilities. Previously, the deterioration of memory, cognition and thinking abilities has been considered as a normal, unmodifiable process as a result of ageing. Nowadays, research has shown that this progression can be delayed and/or slowed down, by improving the overall protection of brain cells during the normal course of ageing.

Normal ageing individuals manifest performance decline in areas of learning, cognition and executive functions. It is suggested that such decline is associated with underlying brain mechanisms, dysregulation of neurotransmitters, neuropeptide & neuroreceptors, oxidative stress, immune system reactions, altered neuroplasticity and loss of synapses, axons, dendrites & neurons in hippocampus.

According to the United States Department of Health and Human Services, Centers for Disease Control and Prevention Report (February 2011) more than 16 million people in the United States are living with cognitive impairment. Age is the greatest risk factor for cognitive impairment, and as the Baby Boomer generation passes the age of 65, the number of people living with cognitive impairment is expected to jump dramatically. An estimated 5.1 million Americans aged 65 years or older may currently have Alzheimer's disease, the most well-known form of cognitive impairment. This number may rise to 13.2 million by the year 2050.

Alzheimer's disease (AD) and related dementias alone are estimated to be the third most expensive disease to treat in the United States. The average Medicaid nursing facility expenditure per state in year 2010 for individuals with Alzheimer's disease was estimated at USD 647 million, not including home and community-based care or prescription drug costs.

The imminent growth in the number of people living with cognitive impairment will place significantly greater demands on our systems of care.

Furthermore, magnesium is one of the seven essential macro-minerals in the world. Magnesium plays an important role in a wide variety of critical cellular processes including oxidative phosphorylation, glycolysis, cellular respiration and protein synthesis.

Magnesium enters the bloodstream after being absorbed from the intestine. Magnesium transport across the cell membranes shows tissue variability and is higher in the heart, liver, kidney, skeletal muscle, red cells, and brain, when compared to other tissues of the body. There is supporting evidence of a correlation between magnesium transport and metabolic activity of the cell. Inorganic forms of magnesium are bound with mineral salt (chloride, oxide, sulfate) and in organic forms, it is bound to molecules such as amino acids (glycinate, taurate) and organic acids (citrate, malate, lactate, aspartate) that are associated with living organisms. The absorption pathways of these different forms are different.

Magnesium depletion, particularly in the hippocampus, appears to represent an important pathogenic factor in AD. A chronic reduction in dietary magnesium impairs memory and the treatment of dementia patients with nutritional magnesium improves memory. An unusual relationship between low magnesium in hippocampal neurons and impairments in learning ability has been demonstrated in aged rats [*Brain research* 322: 167-171].

Recent studies have implicated that magnesium modulates the Amyloid-β Protein Precursor (AβPP) processing and in the presence of high extracellular magnesium levels AβPP processing stimulates the α-secretase cleavage pathway [*J Alzheimers Dis.* 2010; 20(4):1091-106].

Moreover, treatment with a magnesium compound regulates N-methyl-D-aspartate ionotropic glutamate receptors (NMDAR) signaling, prevents synapse loss, and reverses memory deficits in aged rats and AD model rats and magnesium deficiency has been proposed as a risk factor for Type 2 diabetes (T2DM). Therefore, magnesium is involved in AD and diabetes, and may serve as a convergent point that links AD and diabetes.

Further studies indicate that the magnesium ion ($Mg^{2+}$) is a critical factor in controlling synapse density/plasticity.

Further it is reported that magnesium sulfate significantly enhanced the brain magnesium levels, improved synaptic efficacy, and prevented memory and learning impairments through modifications of synaptic proteins that may decrease the risk for cognitive impairment in AD [*PLoS One.* 2014; 9(9): e108645].

It is observed that brain magnesium level and serum $Mg^{2+}$ concentration appears to be significantly lower in AD patients compared with age-matched normal subjects. If so, then simply restoring brain magnesium might beneficiate AD patients. Particularly elevation of brain magnesium prevents/reverses synapse loss and memory deficits in AD subjects.

If brain magnesium levels are reduced under pathological conditions, it might have profound impact on synapse density and memory function. Interestingly, in the hippocampus of AD patients, the total magnesium level is reduced by 18%. Therefore, restoration/elevation of brain magnesium in AD patients might be beneficial for ameliorating the cognitive deficits of AD.

NMDARs are essential for synaptic plasticity and memory functions. Apparently, the Mg ion enrich treatment not only prevents synapse loss, but also restores the functionality of NMDAR signaling in the remaining synapses. Further the elevation of $Mg^{2+}$ can protect NMDARs from Amyloid-β (Aβ)-induced down regulation [*Molecular Brain* volume 7, Article number: 65 (2014)].

The researchers have shown that elevation of brain magnesium by a compound like [Mg-L-threonate (MgLT)] upregulates NMDAR signaling, prevents synapse loss and reverses memory deficits in aged rats [*Neuron.* 2010; 65:165-177].

An increase in magnesium intake enhances memory in young subject, reverses memory decline in aged subject and prevents memory deterioration in a subject of AD.

In this regard, U.S. Pat. No. 9,616,038B2 discloses a method of treating a neurological disorder, comprising oral administration of a composition comprising magnesium threonate.

"Magtein Pro" is an advanced formula that combines the ingredient, (Magnesium L-Threonate), with (Magnesium Acetyl Taurate) to support healthy neurological functions.

However, it is observed that memory problems, which increase with advancing age, is because of aggregation of the protein Amyloid-β (Aβ)-, and is responsible for the loss of neurons in the hippocampus as well as a cause of Alzheimer's disease.

Dysfunction in the clearance of Amyloid β (Aβ) protein and neuroinflammation are two functionally linked pathological aspects of key importance in the development and progression of Alzheimer's disease. The results from Korea Institute of Science and Technology [*Sci Rep.* 2014; 4: 7467] study indicate that taurine may play a role in preventing cognitive impairment in AD-like mouse model. However, the exact mechanism is not clear how taurine induces improvement of abnormal behaviors in AD model mice without the significant inhibition of Aβ amyloidogenesis.

It is further observed that soluble Amyloid-β (Aβ) oligomer potentiates intracellular tau aggregation and shows that oligomeric Aβ specifically exacerbates proteopathic seeding by tau. The effective tau-uptake inhibitor blocks the effect of Aβ on tau uptake.

Therefore, the need arises to find out efficient neuronutrition supplement for slowing down age-related decline in brain capacity by reducing plaque deposition of the Amyloid β peptide and tau protein.

Therefore, the inventors of the present invention have found that homotaurine is one of the best nutrients highlighted for its neuroprotective effects, in a specific area of the brain, the hippocampus, which is the site of memorization and learning.

Accumulations of insoluble deposits of Amyloid β-peptide are major pathological hallmarks of Alzheimer's disease. The proteolytic enzymes involved in its processing are named secretases. β-and γ-secretase liberate by sequential cleavage the neurotoxic Amyloid β-peptide, whereas α-secretase prevents its generation by cleaving within the middle of the amyloid domain.

The progressive accumulation of Amyloid β-peptides associated with a reduced clearance may promote aggregation of Aβ peptides in oligomers and fibrils species, with a powerful toxic effect on neurons responsible for dramatic changes of synaptic plasticity machinery with impaired long-term potentiation (LTP) and prolonged long-term depression (LTD), spine shrinkage and loss, and neuronal degeneration. These changes are supposed to start long before cognitive decline appear, therefore, low Aβ levels could be easily detected in mild cognitive impairment (MCI) patients.

Further, it is observed that the progression of Alzheimer's disease is being monitored by measuring the rate of hippocampal volume loss by means of magnetic resonance imaging (MM). Research suggests that a reduction in hippocampal volume can be detected over a period as short as 6 months, and that such volume loss is associated with cognitive decline and other indicators of Alzheimer disease neuropathology [*Nature Reviews Neurology* volume 5, pages 361-362(2009)].

Homotaurine, or 3-amino-1-propanesulfonic acid, is a natural-source organic compound found in certain seaweeds. Though chemically like taurine, with only one additional carbon atom in its chain, it offers cognitive protection that taurine does not provide. Structurally similar to the neurotransmitter gamma-Aminobutyric acid (GABA), it also has similar effects and may be useful as an anti-convulsant.

Homotaurine or Tramiprosate, is a small aminosulfonate compound that counteracts Aβ fibrillogenesis reducing the toxic effects on neurons. Indeed, in experimental models homotaurine administration induced inhibition of Aβ fibrils formation, reduction of the brain pathologic burden, and formation of physiological LTP [*Neurobiol Aging*. 2007 April; 28(4):537-47].

Further, homotaurine is naturally found in red and green algae, which has been demonstrated to have neuroprotective effects. Moreover, homotaurine supplementation has a positive consequence on hippocampus atrophy and short-term episodic memory loss in individuals at the earliest clinical state of AD, called amnestic mild cognitive impairment (aMCI) [*J Alzheimers Dis*. 2016; 50(3):807-16]. Hippocampus atrophy has also been correlated with the presence of tau protein that builds up as Alzheimer's disease progresses.

Additionally, WO2010/096925A1 relates to methods, materials and compositions for administering homotaurine-supplemented and/or enriched edible material in humans, which is useful in neuroprotection and for improving or preserving cognitive and/or memory functions. Additionally, WO2017083983A1 discloses use of a homotaurine or a homotaurine-enriched edible material for improving mental condition of a non-human animal.

EP3219306A1 relates to a composition for preventing or treating neurodegenerative diseases of the central nervous system or ocular diseases or cognitive disorders, said composition comprising a combination of citicoline and homotaurine in a therapeutically effective amount.

It is also reported that homotaurine supplementation holds anti-inflammatory properties associated with memory improvement in patients with cognitive impairment. [*Front Aging Neurosci*. 2018; 10: 285].

The soluble Aβ oligomers and amyloid plaques alter the function of local neuronal circuits and large-scale networks by disrupting the balance of synaptic excitation and inhibition (E/I balance) in the brain.

These findings motivated the inventors of the present invention to develop potential anti-amyloid therapies, along with Mg enrichment to improve cognitive functions, where the hippocampal volume loss is regulated.

In view of the above prior arts, it is concluded that for better cognitive function there is a need for a combined effect, which imparts synergy to brain functions with significant results.

Accordingly, the inventors of the present invention have performed rigorous experiments and developed nutritional compositions which give synergistic effect for treating cognitive disorders by ameliorating synaptic function simultaneously controlling hippocampal volume loss (HVL) or damage or shrinkage.

OBJECTIVES OF THE INVENTION

The primary objective of the invention is to provide synergistic nutritional compositions for treating neurocognitive disorders.

Another objective of the invention is to provide stable and potent synergistic composition of nutrients for improving cognitive function in a subject.

Further objective of the invention is to provide synergistic combination of therapeutically active cognitive enhancers for improving synaptic health.

Another objective of the invention is to improve cognition, functional ability and behavioral symptoms in a subject with cognitive disorder.

Yet another objective of the invention is to provide nutritional composition with synergistic effect for treating cognitive dysfunction by enhancing synaptic plasticity, synaptic density accompanied with positive effect on hippocampus atrophy and episodic memory loss.

Another objective of the invention is to provide synergistic natural mineral-based remedy for treating neurocognitive disorders through site specific action, with no side effects.

SUMMARY OF THE INVENTION

To meet the above objectives, the inventors of the present invention carried out thorough experiments to establish significant effects of the active ingredients or minerals or chemical elements or metals or nutrients or amino acids or sugar acids present in the composition that improve cognitive function in a subject in need thereof in a safer way.

In an aspect, the invention relates to synergistic nutraceutical compositions comprising therapeutically active nutrients along with pharmaceutically acceptable carriers for treating neurocognitive disorders.

In another aspect, the invention relates to synergistic nutraceutical compositions comprising combination of sugar acid salt of magnesium and sulphur containing amino acid, present in specific weight ratio to enhance synaptic density and brain plasticity with reduction of progressive shrinkage of the hippocampus.

In another aspect, the invention relates to synergistic, nutritional composition comprising combination of magnesium L-threonate (MgLT) and homotaurine (HT) present in specific weight ratio along with pharmaceutically acceptable excipients.

Further, the composition provides significant effect for improving cognitive function with improved bioavailability and efficacy.

In another aspect, the present invention provides synergistic composition for improving cognitive function comprising specific combination of magnesium L-threonate and homotaurine; wherein magnesium L-threonate increases neurotransmitter signaling between neurons by promoting neural plasticity and synaptic density; simultaneously or subsequently homotaurine reduces neuron loss in the hippocampus.

In yet another aspect, the invention relates to a synergistic nutritional composition comprising combination of MgLT which is present in a range of 10-3500 mg, wherein elemental $Mg^{2+}$ present in a range of 1-250 mg and homotaurine which is present in a range of 1-500 mg along with pharmaceutically acceptable excipients/carriers.

In yet another aspect, the invention discloses synergistic nutritional composition useful for treating or controlling cognitive disorders such as magnesium deficiency, mild cognitive impairment (MCI), Alzheimer's disease (AD), Huntington's disease, autism, schizophrenia, cognitive decline, depression, dementia, attention deficit hyperactivity disorder (ADHD), amyotrophic lateral sclerosis (ALS), Parkinson's disease, migraine, anxiety, mood disorder, epilepsy, traumatic brain injury, early stage adult dementia, early Alzheimer's disease, and prodromal Alzheimer's disease.

Abbreviations

L-TAMS: L-Threonic acid magnesium salt
MgLT: Magnesium L-threonate
HT: Homotaurine
MCI: Mild cognitive impairment
AD: Alzheimer's disease
NMDARs: N-methyl-d-aspartate receptors
TNF-α: Tumour necrosis factor α
IL-6: Interleukin 6
BDNF: Brain derived neurotrophic factor Ach: Acetylcholine
DSM-IV-TR: Diagnostic and statistical manual of mental disorders: fourth edition text revision
ADHD: attention deficit hyperactive disorder
ALS: amyotrophic lateral sclerosis
NCD: Neurocognitive disorder
DSM: Diagnostic and Statistical Manual of Mental Disorders
TBI: traumatic brain injury
HIV: human immunodeficiency virus
AβPP: Amyloid-β Protein Precursor
T2D: Type 2 diabetes
Aβ: Amyloid-β
LTP: long-term potentiation
LTD: long-term depression
MRI: magnetic resonance imaging
GABA: gamma-Aminobutyric acid
E/I: excitation and inhibition
GABAA: γ-aminobutyric acid type A
GABAAR: GABAA receptors
HPC: hydroxypropyl cellulose
HPMC: hydroxypropyl methyl cellulose
PVP: polyvinylpyrrolidone
PEG: polyethylene glycol
BHT: butylated hydroxytoluene
BHA: butylated hydroxyanisole
SMB: sodium metabisulfite
PG: propyl gallate
CYS: cysteine
CPCSEA: Committee for the purpose of control and supervision of experiments on animals

DETAILED DESCRIPTION OF THE INVENTION

The invention will now be described in detail in connection with certain preferred and optional embodiments, so that various aspects thereof may be more fully interpreted and comprehended. However, any skilled person or artisan will appreciate the extent to which such embodiments could be generalized in practice.

It is further to be understood that all terminology used herein is for the purpose of describing embodiments only and is not intended to be limiting in any manner or scope. Unless defined otherwise, all technical and scientific expressions used herein have the same meaning as commonly understood by one of ordinary skill in the art to which embodiments of the invention pertain. In describing and claiming the embodiments of the present invention, the following terminology will be used in accordance with the definitions set out below which are known in the state of art.

The singular forms "a", "an", and "the" include plural reference unless the context clearly dictates otherwise. Also, the term "composition" does not limit the scope of the invention for multiple compositions that can be illustrated for best mode of the invention.

The term "pharmaceutically/nutraceutically acceptable salt", as use herein, represents those salts which are within the scope of sound medical judgment, suitable for use in contact with the tissues of humans and animals without undue toxicity, irritation, allergic response and the like and commensurate with a reasonable benefit/risk ratio.

Particularly the term "pharmaceutically acceptable salts" refers to the relatively non-toxic, inorganic, and organic acid addition salts of compounds, amino acid salt, sugar-based salt, alkali or alkaline earth metal salts, as well as solvates, co-crystals, polymorphs and the like of the salts.

All modifications and substitutions that come within the meaning of the description and the range of their legal equivalents are to be embraced within their scope. A description using the transition "comprising" allows the inclusion of other elements to be within the scope of the invention.

In a preferred embodiment, the invention provides novel and stable synergistic nutritional compositions comprising specific combination of magnesium salt of sugar acid and sulfur-containing amino acid along with pharmaceutically acceptable carriers, wherein the magnesium salt of sugar acid is L-threonic acid magnesium salt (L-TAMS) or magnesium L-threonate (MgLT) and sulfur-containing amino acid is homotaurine.

In another embodiment, the invention provides potent and stable synergistic nutritional composition for improving cognitive ability.

The term "cognitive ability" is defined as a "mental capability that involves the ability to reason, plan, solve problems, think abstractly, comprehend complex ideas, learn quickly and learn from experience".

The term "cognitive dysfunction" can be used interchangeably with cognitive impairment, cognitive imbalance, cognitive decline, cognitive deficit, cognitive problems, cognitive instability, cognitive disorders, cognitive issues, cognitive ageing, neurocognitive disorders, synaptic loss and like thereof.

The term "stable" is defined as a composition that is stable upon prolonged storage, as assessed from the content of one or more impurities in the composition. The stability of the nutraceutical composition may be tested in a conventional manner, e.g., by measurement of active ingredients and its degradation products, dissolution, friability, disintegration time, appearance and/or microscopy, e.g., after storage at 25° C. and 60% relative humidity, and/or storage at 40° C. and 75% relative humidity for defined periods of time.

Preferably, the solid compositions of the present invention will be stable for at least 6 or 12 months when kept at a temperature of 25 to 40° C. In a more preferred embodiment, the present nutritional composition is stable over a certain period of time such as 1 year, and preferably 2 years.

"Cognitive enhancers" are a class of substances that can boost brain performance. They are sometimes called nootropics or memory enhancing substances which are used to improve memory, increase mental alertness and concentration as well as boost energy levels and wakefulness.

More particularly, the instant biologically active composition is composed of synergistic combination of magnesium L-threonate and homotaurine, which are present in therapeutically effective amount. The composition exhibits significant cognitive effect with enhanced bioavailability, solubility, stability and therapeutic efficacy.

The improvement in cognitive function is accompanied by synergistic effect of nutrients; wherein magnesium

L-threonate increases neurotransmitter signaling between neurons by promoting neural plasticity and synaptic density; on the other side homotaurine reduces the loss in hippocampal volume.

In another embodiment, the invention provides the nutritional combination, wherein the synergistic effect for improving cognitive function is achieved by concomitant synaptic functioning of cognitive enhancers, wherein one enhancer is MgLT.

According to the invention, magnesium threonate is a salt of magnesium and L-threonate with neuroprotective and cognitive enhancing effects. Magnesium L-threonate or MgLT significantly improves memory and learning ability by enhancing synaptic density and plasticity.

Neural plasticity is also referred as brain plasticity or synaptic plasticity. Plasticity is the brain's ability to change and grow and is fundamental for memory and learning to take place.

"Magnesium threonate" also may be referred to as magnesium L-threonate, chemically known as magnesium (2R,3S)-2,3,4-trihydroxybutanoate, L-Threonic acid Magnesium salt (L-TAMS), or MgLT. It has chemical formula $C_8H_{14}MgO_{10}$ represented below as Formula I.

Formula I

Magnesium L-threonate is the latest magnesium chelate which binds to L-threonate, a vitamin C metabolite. L-threonate is a derivative of L-ascorbic acid 2-phosphate (which in and of itself is a derivative of ascorbic acid, otherwise known as vitamin C). Ascorbic acid is a type of aldonic sugar acid, in which the aldehyde group (—CHO) located at the initial end of an aldose is oxidized. It is prominent therapeutically active mineral chelations of L-threonate, which significantly enhances bioavailability of magnesium in the synaptic region.

Particularly, the term "elemental magnesium" as used in connection with a magnesium-counter ion compound described herein and may refer to a total amount of magnesium that is present as free ion and magnesium that is bound with one or more counter ions particularly sugar acid.

The term "threonate" describes an ester derivative of threonic acid or threonate, or a lactonized threonic acid. Generally, threonate as used in the present invention refers to L-threonate. L-threonic acid is the L-enantiomer of threonic acid, which is a sugar acid or a sugar acid derivative. L-threonic acid is considered to be soluble in water and is acidic in nature. L-threonic acid can be found naturally in foods such as capers, muscadine grapes, black huckleberries, and pecan nuts.

In a further embodiment, the present invention provides synergistic composition, wherein magnesium from L-threonate easily crosses the blood-brain barrier and once it reaches the brain, magnesium increases NMDAR signaling, Brain Derived Neurotrophic Factor (BDNF) expression and synaptic plasticity in the pre-frontal cortex, thereby improving cognitive function.

A compound according to the present invention demonstrates a superior effect on the stimulation and/or restoration of neuronal plasticity for the treatment of a disease or disorder of the central nervous system in a subject by virtue of its dual action. Such a compound according to the present invention, acts firstly, at a very early stage of the neuronal repair (birth of a new neuron) via the activation of the NMDAR receptor and, secondly, acts on the production of the BDNF factor (brain-derived neurotrophic factor) that influences synaptic plasticity in the adult brain.

Magnesium potentiates activation of NMDA receptors and blocks calcium channels, decreasing neuronal hyperexcitation and excitotoxicity.

Hippocampal synapse density is very sensitive to small changes in extracellular $Mg^{2+}$ concentrations. Brain magnesium is supposed to be more stable as the blood brain barrier isolates the brain from daily fluctuations in blood magnesium. Therefore, despite the high sensitivity of the synapses to $Mg^{2+}$ concentration, synapse density is likely to be stable under physiological conditions.

Notably MgLT improves cognitive function in ageing adults, and aids "rejuvenation" of their brains towards normal function for their age.

In yet another embodiment, the present invention provides synergistic nutritional composition comprising therapeutically effective amount of MgLT along with pharmaceutically acceptable salts thereof, wherein MgLT is present in the range of 10-3500 mg, wherein elemental $Mg^{2+}$ is present in the range of 1-200 mg of total composition.

In one additional embodiment, the present invention provides synergistic nutritional composition magnesium L-threonate containing 6 to 9% w/w of elemental magnesium. More particularly 100 mg to 1000 mg unit dose of magnesium salt of L-threonic acid containing 5 mg to 100 mg of elemental magnesium.

In another embodiment, the present invention provides synergistic nutritional composition comprising threonate salt of Mg wherein L-threonic acid acts as counter ion to enhance the bioavailability of Mg and thus improves the synapse density in the brain.

In another embodiment, the invention provides the nutritional combination, wherein the synergistic effect for improving cognitive function is achieved by concomitant administration of another enhancer, particularly sulphur containing amino acid called "homotaurine" that effectively reduces hippocampal volume loss or hippocampal damage or prevents the hippocampus from shrinking.

"Homotaurine" is also known as 3-APS, 3-Amino-1-Propanesulfonic Acid, 3-aminopropane-1-sulfonic Acid, 3-Aminopropanesulfonic Acid, 3-Aminopropylsulfonic Acid, Acide 3-Aminopropanesulfonique, Homotaurin, Homotaurina, or Tramiprosate. It has molecular formula $C_3H_9NO_3S$ represented below as Formula II.

Formula II

Homotaurine represents a major, natural supplement for combating Alzheimer's disease. It interacts with soluble amyloid beta protein, inhibiting the formation of the neurotoxic aggregates that result in amyloid beta plaque deposits in the brain which in turn produce dysfunction and ultimately death of brain cells. Remarkably homotaurine stems the increase in these plaques and reduces their toxic effects on the brain, thus protecting memory and learning function.

In another embodiment, the effective amount of homotaurine in the composition also significantly inhibits the hippocampal volume loss or hippocampal damage induced by neurotoxin like (amyloid-β and tau protein). Further, homotaurine controls brain inflammation during AD progression.

Further damage to the hippocampus is incorporated into the pathological criteria for Alzheimer's disease, and requires at least some neurofibrillary tangles in the hippocampus, and amyloid-β deposition and moderate neuritic infiltrate in association cortices.

Homotaurine is known to act through a double mechanism: the modulatory activity on cortical γ-aminobutyric acid type A (GABAA) receptors, and the anti-amyloid activity.

Besides the anti-amyloid action, homotaurine has direct effects also on neuronal activity as a modulator of excitatory neurotransmission, due to its binding affinity for GABAA receptors (GABAARs). This modulatory action strengthens the potential neuroprotection mechanisms of homotaurine. Such potential neuroprotective effects could be useful for MCI patients to delay progression to cognitive decline.

Particularly homotaurine binds to beta-amyloid proteins, inhibiting the formation of neurotoxic aggregates and consequent plaque deposits which result in the dysfunction and potential death of brain cells. By reducing the toxic effect of these plaques in the brain, homotaurine supplementation thus protects memory and learning functions.

In another embodiment, the invention provides synergistic nutritional composition where neuroprotective effects of homotaurine, against age-related impairments (e.g., altered neuroplasticity and loss of synapses, axons, dendrites & neurons), contribute towards maintaining neuronal health and protecting brain regions involved to control learning, cognition, and executive functions.

In another embodiment, the invention provides synergistic nutritional composition comprising therapeutically effective amount of homotaurine along with pharmaceutically acceptable salts thereof, wherein homotaurine is present in the range of 1-500 mg, preferably in the range of 1-250 mg of total composition.

In another embodiment, the invention provides synergistic nutritional composition wherein the composition comprises therapeutically active exogenous blend of magnesium L-threonate and homotaurine present in suitable weight ratio, along with pharmaceutically acceptable excipients.

More particularly, the present invention provides synergistic effects of combined magnesium L-threonate (L-TAMS) with homotaurine (HT) and salts thereof for treating neurocognitive disorders. The active moieties of the present composition are present in a therapeutically effective amount. The composition imparts significant effect to the subject in need thereof with enhanced bioavailability and efficacy.

In another preferred embodiment, the invention provides a novel, stable and potent synergistic nutritional composition comprising therapeutically active exogenous combination of an effective amount magnesium L-threonate and homotaurine (HT) which are present in weight ratio of 1:0.1 to 1:1 along with pharmaceutically acceptable excipients.

In yet another preferred embodiment, the invention provides novel and stable nutritional compositions for treating neurocognitive disorders comprising exogenous blend of white crystalline magnesium L-threonate and homotaurine present in the weight ratio of 1:0.1 to 1:1, along with pharmaceutically acceptable excipients, wherein the two active ingredients act synergistically to improve cognitive function.

In yet another preferred embodiment, the invention provides novel and stable nutritional compositions for treating cognitive impairment comprising exogenous blend of white crystalline magnesium L-threonate and homotaurine (HT) in weight ratio of 1:0.1 to 1:1, along with pharmaceutically acceptable excipients, wherein the magnesium L-threonate increases neurotransmitter signaling between neurons by promoting neural plasticity and synaptic density; and concurrently homotaurine reduces hippocampal damage induced by neurotoxin like (amyloid-β and tau protein).

In one more embodiment, the invention provides potent and stable synergistic nutritional composition comprising white crystalline magnesium L-threonate present in a range of 50% to 95% by weight of the total composition.

In another embodiment, the invention provides potent and stable synergistic nutritional composition comprising white crystalline homotaurine which is present in a range of 5% to 50% by weight of the total composition.

In another embodiment, the invention provides potent and stable synergistic nutritional composition useful for treating neurocognitive disorders.

Particularly the disorders are including but not limited to magnesium deficiency, mild cognitive impairment (MCI), Alzheimer's disease (AD), Huntington's disease, autism, schizophrenia, cognitive decline, depression, dementia, attention deficit hyperactivity disorder (ADHD), amyotrophic lateral sclerosis (ALS), Parkinson's disease, migraine, anxiety, mood disorder, epilepsy, traumatic brain injury, early-stage adult dementia, early Alzheimer's disease, and prodromal Alzheimer's disease.

The term "therapeutically effective amount" denotes an amount that reduces the risk, potential, possibility or occurrence of a disease or disorder, or provides advanced alleviation, mitigation, and/or reduction or restoration or modulation, and regulation of at least one indicator/biomarker (e.g., blood or serum CRP level), and/or minimizes at least one clinical symptom related to cognitive dysfunction or impairment.

Particularly the present synergistic nutritional composition upon oral administration of an effective dose improves the expression of biomarkers like BDNF and Acetylcholine.

Brain-derived neurotrophic factor (BDNF) is a pleiotropic protein member of the neurotrophic factor. Acetylcholine is a chemical messenger, or neurotransmitter, that plays an important role in brain and muscle function.

In yet another embodiment, the invention provides the novel and stable nutritional composition wherein the oral administration of the effective dose of the composition increases the BDNF expression by 85% to 95% over disease control.

On the contrary, the present synergistic nutritional composition upon oral administration of effective dose reduces the accumulation of abnormal aggregates composed of two proteins: Amyloid beta (Aβ) and tau. Amyloid-β peptides are proteolytic fragments of the transmembrane amyloid precursor protein, whereas tau is a brain-specific, axon-enriched microtubule-associated protein.

In yet another embodiment, the invention provides the novel and stable nutritional composition wherein the oral administration of the effective dose of the composition decreases the Tau protein expression by 65 to 70% over disease control.

Neuroinflammation plays an important role in Alzheimer's disease (AD). During this process, activated microglia release pro-inflammatory cytokines such as interleukin (IL)-1α, IL-1β, IL-6, and tumor necrosis factor α (TNFα) that participate in neuron damage.

Interestingly, the present synergistic nutritional composition upon oral administration of the effective dose lowers the elevated level of inflammatory cytokines like TNFα and IL-6.

In further embodiment, the invention provides the novel and stable nutritional composition wherein the oral administration of the effective dose of the composition reduces the TNFα cytokine expression by 60% to 65% over disease control.

In another embodiment, the invention provides the novel and stable nutritional composition wherein the oral administration of an effective dose of the composition improves latency time by 2 to 3 folds over disease control.

The term "subject in need thereof" pertains to subject preferably mammal, more preferably human suffering or suspected with cognitive decline or memory loss.

In the context of the present invention, the term "treatment" relates to alleviate, mitigate, prophylactic treatment, attenuate, manage, regulate, modulate, control, minimize, lessen, decrease, down regulate, up regulate, moderate, inhibit, restore, suppress, reverse, limit, block, decrease, prevent, inhibit, stabilize, ameliorate or cure, heal the high tau deposition and synaptic density loss observed in patients with neurocognitive disorder.

Notably, the present synergistic composition is non-hazardous, non-toxic, food ingredient and safe for human consumption without any adverse effects, therefore the present nutritional composition can also be used under preventive therapy/adjuvant therapy/add-on therapy/combination/adjunctive therapy in a subject in need thereof.

Certain compounds of the present invention can exist in unsolvated forms as well as solvated forms, including hydrated forms. Further some compounds of the present invention can exist in multiple crystalline or amorphous forms ("polymorphs"). Compounds of the present invention can exist in geometric, or enantiomeric, or stereoisomeric forms.

The present invention contemplates all such compounds, including dextrorotatory and levorotatory isomers. All such isomers, as well as mixtures thereof, are intended to be included in this invention.

As used herein, the term "pharmaceutically acceptable carriers, diluents or excipients" is intended to mean, without limitation, any adjuvant, carrier, excipient, sweetening agent, diluents, preservative, dye/colorant, flavor enhancer, surfactant, wetting agent, dispersing agent, suspending agent, stabilizer, isotonic agent, solvent, emulsifier, or encapsulating agent, encapsulating polymeric delivery systems or polyethyleneglycol matrix, which is acceptable for use in the subject, preferably humans. Excipients may also include, for example: antiadherents, antioxidants, binders, coatings, compression aids, disintegrants, dyes (colors), emollients, emulsifiers, fillers (diluents), film formers or coatings, fragrances, glidants (flow enhancers), lubricants, preservatives, sorbents, suspending or dispersing agents, sweeteners, surfactant, anticaking agent, food additives, or waters of hydration, salts.

In another embodiment, the invention relates to synergistic medicinal composition, which can be prepared in a manner well known in the pharmaceutical art, and can be administered by a variety of routes, depending upon whether local or systemic treatment is desired and upon the area to be treated. The preferable route of administration includes but not limited to sublingual, rectal, topical, parenteral, nasal or oral.

In some embodiment, the present synergistic medicinal composition can be administered to the subject in need thereof, in the form which is suitable for oral use, such as a tablet, capsule (in the form of delayed release, extended release, sustained release, enteric coated release); hard gelatin capsules, soft gelatin capsules in an oily vehicle, veg capsule, hard or soft cellulose capsule, granulate for sublingual use, effervescent or carbon tablets, aqueous or oily solution, suspension or emulsion, encapsulate, matrix, coat, beadlets, nanoparticles, caplet, granule, particulate, agglomerate, spansule, chewable tablet, lozenge, troche, solution, suspension, rapidly dissolving film, elixir, gel, tablets, pellets, granules, capsules, lozenges, aqueous or oily solutions, suspensions, emulsions, sprays or reconstituted dry powdered form with a liquid medium or syrup; for topical use including transmucosal and transdermal use, such as a cream, ointment, gel, aqueous or oil solution or suspension, salve, parch or plaster; for nasal use, such as a snuff nasal spray or nasal drops; for vaginal or rectal use, such as a suppository; for administration by 5 inhalation, such as a finely divided powder or a liquid aerosol; for sub-lingual or buccal use, such as a tablet, capsule, film, spray. Further the composition can be formulated for parenteral use including intravenous, subcutaneous, intramuscular, intravascular, infusion, intraperitoneal, intracerebral, intracerebroventricular, or intradermal.

Formulations of the present invention suitable for oral administration can be presented as discrete units such as capsules (e.g., soft-gel capsules), cachets or tablets each containing a predetermined amount of the active ingredient; as a powder or granules; as a solution or a suspension in an aqueous liquid or a non-aqueous liquid, syrup; or as an oil-in-water liquid emulsion or a water-in-oil liquid emulsion. The active ingredients can also be presented in the form of a bolus, electuary or paste, nutritional bar, energy bars (candy bars), powder, or granule sachet.

Further, the present composition can be formulated in the form of age-appropriate pediatric oral dosage forms such as syrup, minitablets, chewable formulations, orodispersible films, or orodispersible tablets. It can also be prepared in the form of snack, chocolate bars or other confectionery food products.

In another embodiment, the synergistic composition of the present invention is non-toxic, cost effective, enriched with nutrients or biomolecules, and provides safeguard against problems associated with neurotransmission without any adverse/side effect.

In another embodiment of the invention, the diluents are selected from starches, hydrolyzed starches, partially pregelatinized starches, anhydrous lactose, cellulose powder, lactose monohydrate, sugar alcohols such as sorbitol, xylitol and mannitol, silicified microcrystalline cellulose, ammonium alginate, calcium carbonate, calcium lactate, dibasic calcium phosphate (anhydrous/dibasic dehydrate/tribasic), calcium silicate, calcium sulphate, cellulose acetate, corn starch, pregelatinized starch, dextrin, β-cyclodextrin, methylated-β-cyclodextrin, dextrates, dextrose, erythritol, ethyl cellulose, fructose, fumaric acid, glyceryl palmitostearate, magnesium carbonate, magnesium oxide, maltodextrin, maltose, medium-chain triglycerides, polydextrose, polymethacrylates, sodium alginate, sodium chloride, sterilizable maize, sucrose, sugar spheres, talc, trehalose, xylitol, vehicles like petrolatum, dimethyl sulfoxide and mineral oil or the like.

In some embodiment of the invention, the diluent in the composition/formulation is present in a range of 1% to 30% by weight of the total composition/formulation.

In yet another embodiment of the invention, the binder is selected from disaccharides such as sucrose, lactose, polysaccharides and their derivatives like starches, cellulose, or modified cellulose such as microcrystalline cellulose and cellulose ethers such as hydroxypropyl cellulose (HPC); hydroxypropyl methyl cellulose (HPMC); sugar alcohols such as xylitol, sorbitol, or mannitol; protein like gelatin; synthetic polymers such as polyvinylpyrrolidone (PVP), polyethylene glycol (PEG), starch, acacia, agar, alginic acid, calcium carbonate, calcium lactate, carbomers, carboxymethylcellulose sodium, carrageenan, cellulose acetate phthalate, chitosan, co-povidone, corn starch, pregelatinized starch, cottonseed oil, dextrates, dextrin, dextrose, ethyl cellulose, guar gum, hydrogenated vegetable oil, mineral oil, hydroxyethyl cellulose, hydroxymethyl cellulose, hydroxyl ethyl methyl cellulose, hydroxypropyl cellulose, inulin, cellulose, methyl cellulose, polyvinylpyrrolidone and polyethylene glycol, lactose, liquid glucose, hypromellose, magnesium aluminum silicate, maltodextrin, maltose, methylcellulose, microcrystalline cellulose, pectin, poloxamer, polydextrose, polymethacrylates, povidone, sodium alginate, stearic acid, sucrose, sunflower oil, various animal vegetable oils, and white soft paraffin, paraffin, flavorants, colorants and wax.

In further embodiment of the invention, the binder in the composition/formulation is present in a range of 0.1% to 40% by weight of the composition/formulation.

In a preferred embodiment of the invention, the amount of binder is present in a range of 0.1% to 25% by weight of the composition/formulation.

In some embodiment, the antioxidant is selected from tocopherol (vitamin E), sesamol, guaiac resin, methionine, beta-carotene, lycopene, lutein, zeaxanthin, butylated hydroxyanisole (BHA), butylated hydroxytoluene (BHT), sodium ascorbate, sodium metabisulfite (SMB), 1-carnosine, propyl gallate (PG), tertiary butyl hydroquinone, cysteine (CYS), citric acid, tartaric acid, phosphoric acid and ascorbic acid.

In some embodiment of the invention, the amount of antioxidant in the composition/formulation is present in the range of 0.1% to 10% by weight of the composition/formulation.

In a preferred embodiment of the invention, the amount of antioxidant is present in a range of 0.1% to 5.0% by weight of the composition/formulation.

In another embodiment of the invention, the lubricant is selected from magnesium stearate, zinc stearate, calcium stearate, glycerin monostearate, glyceryl behenate, glyceryl palmitostearate, hydrogenated castor oil, hydrogenated vegetable oil, light mineral oil, magnesium lauryl sulphate, medium-chain triglycerides, mineral oil, myristic acid, palmitic acid, poloxamer, polyethylene glycol, sodium benzoate, sodium chloride, sodium lauryl sulphate, sodium stearyl fumarate, stearic acid, talc, potassium, or sodium benzoate or the like.

In some embodiment of the invention, the lubricant in the composition/formulation is present in a range of 0.1% to 10.0% by weight of the total composition/formulation.

In another embodiment of the invention, the solubilizing agent is selected from polysorbate 80, sodium lauryl sulphate, anionic emulsifying wax, nonionic emulsifying wax, glyceryl monooleate, phospholipids, polyoxyethylene alkyl ethers, polyoxyethylene castor oil derivatives, polyoxyethylene sorbitan fatty acid esters, polyoxyethylene stearates, polyoxylglycerides, sorbitan esters, triethyl citrate, vitamin E, polyethylene glycol succinate, microcrystalline cellulose, carboxymethylcellulose sodium, diethanolamine, ethylene glycol palmitostearate, glycerin monostearate, hypromellose, hypromellose, acetate succinate, lecithin, polyethylene alkyl ethers, aluminum oxide, poly(methylvinyl ether/maleic anhydride), calcium carbonate, crospovidone, cyclodextrins, fructose, hydroxypropyl betadex, oleyl alcohol, povidone, benzalkonium chloride, benzethonium chloride, benzyl alcohol, benzyl benzoate, cetylpyridinium chloride, inulin, meglumine, poloxamer, pyrrolidone, sodium bicarbonate, starch, stearic acid, sulfobutylether beta cyclodextrin, tricaprylin, triolein, docusate sodium, glycine, alcohol, self-emulsifying glyceryl monooleate, cationic benzethonium chloride, cetrimide, xanthan gum, lauric acid, myristyl alcohol, butylparaben, ethylparaben, 15 methylparaben, propylparaben, sorbic acid or the like.

In another embodiment of the invention, the amount of solubilizing agent or surfactant in the composition/formulation ranges from 0.1% to 10% by weight of the composition/formulation.

In a preferred embodiment of the invention, the solubilizing agent or surfactant is present in a range of 0.1% to 5.0% by weight of the composition/formulation.

In some embodiment of the invention, the glidant is selected from colloidal silicon dioxide, magnesium stearate, fumed silica (colloidal silicon dioxide), starch, talc, calcium phosphate tribasic, cellulose powdered, hydrophobic colloidal silica, magnesium oxide, zinc stearate, magnesium silicate, magnesium trisilicate, silicon dioxide or the like.

In another embodiment of the invention, the glidant in the composition/formulation is present in a range of 0.1% to 5.0% by weight of the total composition/formulation.

In some embodiment of the invention, the stabilizers are selected from the group consisting of alginate, agar, carrageen, gelatin, guar gum, gum arabic, locust bean gum, pectin, starch, xanthan gum, trehalose and likewise.

In some embodiment of the invention, the stabilizer in the composition/formulation is present in a range of 0.1% to 8.0% by weight of the total composition/formulation.

In a preferred embodiment of the invention, the amount of stabilizer is present in a range of 0.1% to 5.0% by weight of the composition/formulation.

In some embodiment of the invention, the plasticizers are added to coating formulations selected from the group propylene glycol, glycerol, glyceryl triacetate (triacetin), triethyl citrate, acetyl triethyl citrate, diethyl phthalate, actetylated monoglycerides, castor oil, mineral oil and like thereof.

In some embodiment of the invention, the plasticizer in the composition/formulation is present in a range of 0.1% to 5.0% by weight of the total composition/formulation.

In some embodiment of the invention, the solvent is selected from water, alcohol, isopropyl 10 alcohol, propylene glycol, mineral oil, benzyl alcohol, benzyl benzoate, flavored glycol, carbon dioxide, castor oil, corn oil (maize), cottonseed oil, dimethyl ether, albumin, dimethylacetamide, ethyl acetate, ethyl lactate, medium-chain triglycerides, methyl lactate, olive oil, peanut oil, polyethylene glycol, polyoxyl, castor oil, propylene carbonate, pyrrolidone, safflower oil, sesame oil, soybean oil, sunflower oil, water-miscible solvents, organic polar or non-polar solvents or mixtures thereof.

In a preferred embodiment of the invention, the solvent in the composition/formulation is used in a quantity sufficient to make the weight of the composition/formulation 100% by weight.

The additional additives include a polymer, a plasticizer, a sweetener, and a powdered flavor, a preservative, a colorant, a surfactant, and other excipients. The powdered flavor composition includes a flavourant associated with a solid carrier. Coating materials such as synthetic polymers, shellac, corn protein (zein) or other polysaccharides, gelatin, fatty acids, waxes, shellac, plastics, and plant fibers and like thereof are used.

In a preferred embodiment of the invention, the additives are used in a range of 1% to 20% w/w of unit dose.

In a preferred embodiment of the invention, the amount of additives are present in a range of 0.1% to 10% by weight of the composition/formulation.

In yet another embodiment, the invention provides a synergistic nutritional composition comprising a therapeutic blend of a biotin-manganese complex and a stabilized oxaloacetate along with pharmaceutical excipients, wherein the pharmaceutical excipients are selected from a diluent, a binder, a lubricant, a glidant, an additive, a surfactant, a stabilizer or mixtures thereof.

In a preferred embodiment, the invention provides the novel and stable nutritional composition wherein the pharmaceutically acceptable excipients are selected from a group consisting of the diluent is present in a range of 1 to 30%; the binder present is present in a range of 0.1 to 25%; the lubricant is present in a range of 0.1 to 10.0%; the glidant is present in a range of 0.1 to 5.0%; the additive is present in a range of 1 to 10%; the surfactant is present in a range of 0.1 to 5.0%; the stabilizer is present in a range of 0.1 to 5.0%; %; the antioxidant is present in a range of 0.1 to 5.0%; and the plasticizer is present in a range of 0.1 to 5.0%; by weight of total composition.

In another preferred embodiment, the present medicinal composition/formulation is formulated for oral administration. Specifically, the solid medicinal compositions, are in the form of tablets, capsules, pills, hard capsules filled with liquids or solids, soft capsules, sachets, powders, granules, suspensions, solutions, or modified release formulations. Formulations of the present invention suitable for oral administration are presented as discrete units such as capsules (e.g., soft-gel capsules, hard-gel capsule), cachets or tablets each containing a predetermined amount of the active ingredient; as a powder or granules; as a solution or a suspension in an aqueous liquid or a non-aqueous liquid, syrup; or as an oil-in-water liquid emulsion or a water-in-oil liquid emulsion.

In further embodiment compositions containing compounds of the present invention, can be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt thereof.

The magnitude of a prophylactic or therapeutic dose typically varies with the nature and severity of the condition to be treated and the route of administration. The dose, and perhaps the dose frequency, will also vary according to the age, body weight and response of the individual patient.

In general, the total daily dose (in single or divided doses) ranges from about 1 mg per day to about 2500 mg per day, preferably about 10 mg per day to about 1000 mg per day. In some embodiments, the total daily dose can range from about 5 mg to about 4000 mg per day, and preferably about 5 mg to about 2000 mg per day.

In certain embodiments, the invention provides the potent synergistic medicinal composition wherein the effective unit dose for an oral administration is formulated in a range of 10 to 1000 mg.

It is further recommended that children, patients over 60 years old, initially receive low doses and that the dosage be titrated based on individual physiological responses and/or pharmacokinetics. It can be necessary to use dosages outside these ranges in some cases, as will be apparent to those in the art. The present composition can be used as infant formula as well as adult formula by varying the concentration of active ingredients. Further, it is noted that the dietician or nutritionist or certified physician knows how and when to interrupt, adjust or terminate therapy in conjunction with an individual patient's response.

The use of any and all examples, or exemplary language (e.g., such as) provided herein, is intended merely to better illuminate the invention, and does not pose a limitation on the scope of the invention unless otherwise claimed.

Various other examples of compositions and modifications or adaptations thereof can be devised by a person skilled in the art after reading the foregoing preferred embodiments without departing from the scope of the invention. All such further examples, modifications and adaptations are included within the scope of the invention.

It will be appreciated by those versed in the art that the present invention makes available novel and useful nutraceutical compositions and nutraceutical acceptable salts thereof, which have neuroprotective effects in several administration forms. Also, it will be understood by those with knowledge in the dietary supplement and nutraceutical art, that many embodiments of this invention may be made without departing from the scope of the invention, and the invention is not to be construed as limited, as it embraces all equivalents therein.

The invention may be further illustrated by the following examples, which are for illustrative purposes only and should not be construed as limiting the scope of the invention in anyway.

The present disclosure is therefore to be considered as in all respects illustrative and not restrictive, the scope of the invention being indicated by the appended claims and examples, and all changes or alterations which come within the ambit of equivalency are intended to be encompassed therein.

EXAMPLES

Having described the basic aspects of the present invention, the following non-limiting examples illustrate specific embodiments thereof. Those skilled in the art will appreciate that many modifications may be made in the invention without changing the scope of the invention.

Example-1

| i. Composition 1: Synergistic blend | |
|---|---|
| Ingredient | w/w % |
| Magnesium L-Threonate containing 8% w/w elemental Mg | 50 to 95% |
| Homotaurine | 5 to 50% |

| ii. Composition 2: Tablet/Capsule | |
|---|---|
| Ingredient | w/w % unit dose |
| Magnesium L- Threonate | 50 to 95% |
| Homotaurine | 5 to 50% |
| Excipient | 5-20% |
| Average Weight | 100% |
| Average weight in mg | 300-500 mg |

| iii. Composition 3: Tablet/Capsule | |
|---|---|
| Ingredient | w/w % unit dose |
| Magnesium L- Threonate | 50-95% |
| Homotaurine | 5-50% |
| Diluents | 1-10% |
| Binders | 0.5-5% |
| Glidants | 0.5-5% |
| Lubricants | 0.5-5% |
| Stabilizers | 0.1-10% |
| Additives | 1-10% |
| Antioxidant | 0.1-5% |
| Solvents | QS |

| iv. Composition 4: Tablet/Capsule | |
|---|---|
| Ingredient | mg per unit dose |
| Magnesium L-Threonate | 250 |
| Homotaurine | 50 |
| Magnesium Stearate | 1-10 |
| Hydroxypropyl Methylcellulose | 1-10 |
| Microcrystalline Cellulose | 1-20 |
| PVP K-30 | 5-10 |
| Methylated-β-cyclodextrin | 1-10 |
| Polysorbate 80 | 1-10 |
| Mannitol | 1-20 |
| Propylene Glycol | QS |
| Water | QS |
| Average weight | 300-400 mg |

| v. Composition 5: Tablet/Capsule | |
|---|---|
| Ingredient | mg per unit dose |
| Magnesium L-Threonate | 350 |
| Homotaurine | 50 |
| Sodium ascorbate | 1-10 |
| Microcrystalline Cellulose | 2-20 |
| Silicon dioxide | 5-15 |
| Hydroxypropyl Methylcellulose | 2-10 |
| Magnesium citrate | 2-10 |
| PVP K-30 | 5-10 |
| Talc | 1-10 |
| Tween 80 | 1-10 |
| Mannitol | 5-20 |
| Alcohol | QS |
| Water | QS |
| Average weight | 420-500 mg |

| vi. Composition 6: Tablet/Capsule | |
|---|---|
| Ingredient | mg per unit dose |
| Magnesium L-Threonate | 250 |
| Homotaurine | 50 |
| Sodium alginate | 1-10 |
| Microcrystalline Cellulose | 2-20 |
| Silicon dioxide | 5-15 |
| Hydroxypropyl Methylcellulose | 2-10 |
| Stearic acid | 2-10 |
| Dibasic calcium phosphate | 1-20 |
| Starch | 5-10 |
| Talc | 1-10 |
| Tween 80 | 1-10 |
| polydextrose | 5-20 |
| Water | QS |
| Average weight | 370-450 mg |

| vii. Composition 7: Tablet/Capsule | |
|---|---|
| Ingredient | mg per unit dose |
| Magnesium L-Threonate | 50 |
| Homotaurine | 50 |
| Microcrystalline Cellulose | 1-10 |
| Silicon dioxide | 1-10 |
| Ethyl Cellulose | 1-10 |
| Hydroxypropyl Methylcellulose | 1-10 |
| Magnesium Stearate | 2-10 |
| Polyvinylpyrrolidone | 1-10 |
| Talc | 1-10 |
| Polysorbate 20 | 1-10 |
| Mannitol | 1-10 |
| IPA | QS |
| Water | QS |
| Average weight | 200-250 mg |

| viii. Composition 8: Tablet/Capsule | |
|---|---|
| Ingredient | mg per unit dose |
| Magnesium L-Threonate | 100 |
| Homotaurine | 25 |
| Silicon Dioxide | 1-10 |
| Medium-chain triglycerides | 1-5 |
| Microcrystalline Cellulose | 2-20 |
| Dibasic Calcium Phosphate | 2-20 |
| Magnesium Stearate | 2-10 |
| Croscarmellose sodium | 2-10 |
| Polyvinylpyrrolidone | 1-20 |
| Talc | 1-10 |
| Starch | 1-10 |
| Sodium ascorbate | 1-10 |
| Propylene glycol | 1-10 |
| Water | QS |
| Average weight | 150-200 mg |

| ix. Composition 9: Tablet/Capsule | |
|---|---|
| Ingredient | mg per unit dose |
| Magnesium L-Threonate | 250 |
| Homotaurine | 25 |
| Microcrystalline Cellulose | 1-10 |
| Colloidal silicon dioxide | 1-10 |
| Hydroxypropyl Methylcellulose | 1-10 |
| Magnesium Stearate | 2-10 |
| Polyvinylpyrrolidone | 1-10 |
| Calcium Phosphate | 1-10 |
| Ascorbic Acid | 1-10 |
| Polysorbate 20 | 1-10 |
| Talc | 1-5 |

-continued ix. Composition 9: Tablet/Capsule

| Ingredient | mg per unit dose |
|---|---|
| Sucrose | 1-10 |
| Mannitol | 1-10 |
| Glycerol | 1-10 |
| Average weight | 280-350 mg | x. Composition 10: Tablet/Capsule

| Ingredient | mg per unit dose |
|---|---|
| Magnesium L-Threonate | 500 |
| Homotaurine | 50 |
| Microcrystalline Cellulose | 1-10 |
| Silicon dioxide | 1-10 |
| Hydroxypropyl Methylcellulose | 1-10 |
| Magnesium Stearate | 2-10 |
| Zinc Stearate | 1-5 |
| Polyvinylpyrrolidone | 1-10 |
| Mineral Oil | 1-10 |
| Sodium benzoate | 1-10 |
| Ascorbic Acid | 1-10 |
| Polysorbate 20 | 1-10 |
| Talc | 1-5 |
| Dextrose | 1-10 |
| Mannitol | 1-10 |
| Water | QS |
| Average weight | 550-625 mg |

The present composition is stable for 24 months under the accelerated condition [40° C., 75% RH], where the purity of the active ingredients is above 97%.

Example 2: Animal Study

"Evaluation of test substance on scopolamine induced memory deficit (Alzheimer's disease) in Swiss albino mice".
Animal Welfare
Study is approved by the Institutional Animal ethics committee and committee for the purpose of control and supervision of experiments on animals (CPCSEA).
Test System Details:
  Test Species: Mice
  Strain: Swiss Albino Mice
  Sex: Male/Female
  Age:8-10 Weeks
  Body Weight: 25-30 gms
  Source: In House Breed
  Total No. of Animals: 42 Animals (7 Groups of 6 Animals Each)
Animal House Conditions
  Lighting: 12/12-Hour Light-Dark Cycle
  Temperature: 22±3° C.
  Relative Humidity: 30 to 70%
  Feed: Normal Chow Diet (Purina Lab Diet 5L79 Rat and Mouse 18%) (PMI Nutrition International).
  Drinking water: Mice were provided with ad libitum drinking water passed through water filter system in autoclaved poly propylene bottles.
Housing Conditions:
  Three mice/cage were housed in autoclaved polypropylene cages using autoclaved paddy husk as the bedding material. Each cage was fitted with top grill having provision for keeping rodent feed and water bottle.
  Vehicle details: 0.5% of Carboxy Methyl Cellulose sodium was used as a vehicle for test formulation Group, Designation and Dose Levels:

TABLE 1

Animal grouping and treatment details

| Groups | Group Description | Human Dose | No. of animals |
|---|---|---|---|
| Group 1 | Normal control | Vehicle | 6 |
| Group 2 | Disease Control | Scopolamine | 6 |
| Group 3 | Reference standard | Donepezil-5 mg | 6 |
| Group 4 | Test - L-TAMS | Proposed dose-250 mg | 6 |
| Group 5 | Test - HT | Proposed dose- 50 mg | 6 |
| Group 6 | Test - L-TAMS:HT | [Low ratio 250 mg:50 mg] | 6 |
| Group 7 | Test - L-TAMS:HT | [High ratio 50 mg:50 mg] | 6 |

Study Procedure:
Induction of Amnesia—
  Amnesia was induced by using the scopolamine injection. Scopolamine is an anti-cholinergic and is an attractive amnesic agent for discerning the action of candidate anti-amnesic drugs.
  Scopolamine is a non-selective postsynaptic muscarinic receptor blocker and can cause cognitive impairments in rodents and humans via decreasing the effectiveness of ACH in the CNS in animals and humans. Scopolamine can induce significant deficits in cognitive performance on behavioral tests which make it a valid pharmacological model for inducing cognitive deficits.
  In this study to evaluate the cognitive effect, the mice were injected with scopolamine intraperitoneally once daily with the test sample to induce memory deficits. Behavioral studies were conducted to examine the learning and memory ability by using following tests—
  Spatial learning test-T-maze
  Pole climbing
Administration and Procedure—
  All the animals were acclimatized for at least 5 days under controlled environmental condition. Total 42 animals were divided into seven groups consisting of 6 animals per group.
  Normal control (G1) group receiving vehicle, disease control (G2) group receiving scopolamine injection only, standard group (G3) receiving donepezil and treatment groups (G4, G5, G6 & G7) were treated with the test substance followed by the scopolamine injection. Standard and test substances were administered orally 30 mins before scopolamine injection. All the treatments were administered daily for 14 consecutive days. The following behavioral test were conducted at the end of the treatment,
  Spatial learning test (T-maze test)
  Pole climbing method
Biochemical Assays—
  The following assays were performed,
  Tau pathology: Tau protein
  Neurotrophic factors: Brain-derived neurotrophic factor (BDNF)
  Neuro-inflammation cytokines: TNF-α and IL-6
  Cholinergic dysfunction: Acetylcholine
  All data including body weight, feed consumption, were analyzed statistically using Graph-Pad Prism Software, version 5.01. All values were expressed as Mean±SD. The significant difference between the treatment and control group were estimated using one-way analysis of variance (ANOVA) with Dunnett's test. All results of the statistical analysis were summarized in separate tables.

Results

TABLE 2

Effect of test substances on Mice body weight

| Group | Treatment | Body Weight (gm) Initial | End of the treatment |
|---|---|---|---|
| Group 1 | Normal control | 27.91 ± 3.0 | 29.67 ± 2.5 |
| Group 2 | Disease Control | 27.33 ± 2.8 | 28.08 ± 3.0 |
| Group 3 | Reference standard | 28.17 ± 2.5 | 29.50 ± 2.0 |
| Group 4 | Test - L-TAMS | 27.00 ± 2.5 | 28.67 ± 2.4 |
| Group 5 | Test - HT | 28.17 ± 2.5 | 29.75 ± 2.2 |
| Group 6 | Test - L-TAMS:HT | 26.83 ± 1.8 | 28.24 ± 2.7 |
| Group 7 | Test - L-TAMS:HT | 28.17 ± 2.8 | 29.67 ± 2.5 |

TABLE 3

Effect of test substances on Mice Feed Consumption

| Group | | Feed Consumption (gm) 0 day | Week 4 |
|---|---|---|---|
| Group 1 | Normal control | 3.47 | 4.05 |
| Group 2 | Disease Control | 3.70 | 4.42 |
| Group 3 | Reference standard | 3.98 | 4.68 |
| Group 4 | Test - L-TAMS | 3.68 | 4.92 |
| Group 5 | Test - HT | 3.83 | 4.88 |
| Group 6 | Test - L-TAMS:HT | 4.03 | 4.77 |
| Group 7 | Test - L-TAMS:HT | 4.07 | 4.88 |

TABLE 4

T-Maze test (Time spent in the preferred and discriminated (sec) arm)

| Groups | 1 | 2 | 3 | 4 | 5 | 6 | Average |
|---|---|---|---|---|---|---|---|
| Preferred Arm | | | | | | | |
| Group 1 | 80 | 75 | 77 | 82 | 78 | 79 | 78.50 |
| Group 2 | 68 | 65 | 68 | 68 | 65 | 64 | 66.33 |
| Group 3 | 115 | 125 | 121 | 131 | 110 | 122 | 120.67 |
| Group 4 | 108 | 110 | 107 | 109 | 104 | 101 | 106.50 |
| Group 5 | 109 | 102 | 106 | 108 | 105 | 104 | 105.67 |
| Group 6 | 154 | 156 | 138 | 142 | 151 | 149 | 148.33 |
| Group 7 | 146 | 153 | 140 | 148 | 150 | 152 | 148.17 |
| Discriminated Arm | | | | | | | |
| Group 1 | 77 | 73 | 74 | 78 | 71 | 72 | 74.17 |
| Group 2 | 110 | 125 | 120 | 115 | 110 | 112 | 115.33 |
| Group 3 | 60 | 55 | 56 | 53 | 55 | 56 | 55.83 |
| Group 4 | 57 | 58 | 61 | 59 | 60 | 59 | 59.00 |
| Group 5 | 60 | 58 | 61 | 62 | 60 | 63 | 60.67 |
| Group 6 | 38 | 40 | 34 | 38 | 41 | 42 | 38.83 |
| Group 7 | 45 | 39 | 37 | 40 | 36 | 41 | 39.67 |

TABLE 5

T-Maze test (Latency time (sec) arm)

| Groups | 1 | 2 | 3 | 4 | 5 | 6 | Average |
|---|---|---|---|---|---|---|---|
| Group | | | | | | | |
| Group 1 | 14 | 13 | 14 | 11 | 13 | 14 | 13.17 |
| Group 2 | 28 | 27 | 27 | 28 | 28 | 26 | 27.33 |
| Group 3 | 20 | 19 | 20 | 18 | 18 | 19 | 19.00 |
| Group 4 | 17 | 18 | 20 | 23 | 21 | 17 | 19.33 |
| Group 5 | 20 | 19 | 18 | 19 | 17 | 20 | 18.83 |
| Group 6 | 8 | 7 | 6 | 8 | 8 | 7 | 7.33 |
| Group 7 | 9 | 7 | 6 | 9 | 8 | 8 | 7.83 |

TABLE 6

T-Maze test (Number of entries in preferred and discriminated arms)

| Groups | 1 | 2 | 3 | 4 | 5 | 6 | Average |
|---|---|---|---|---|---|---|---|
| Preferred Arm | | | | | | | |
| Group 1 | 4 | 5 | 4 | 4 | 3 | 2 | 3.67 |
| Group 2 | 2 | 2 | 2 | 1 | 1 | 2 | 1.67 |
| Group 3 | 5 | 6 | 4 | 5 | 6 | 5 | 5.17 |
| Group 4 | 4 | 5 | 6 | 5 | 4 | 5 | 4.83 |
| Group 5 | 6 | 4 | 5 | 4 | 5 | 3 | 4.50 |
| Group 6 | 9 | 8 | 9 | 9 | 10 | 8 | 8.83 |
| Group 7 | 8 | 9 | 9 | 8 | 9 | 8 | 8.50 |
| Discriminated Arm | | | | | | | |
| Group 1 | 3 | 2 | 3 | 1 | 2 | 3 | 2.33 |
| Group 2 | 5 | 7 | 7 | 6 | 6 | 7 | 6.33 |
| Group 3 | 3 | 2 | 3 | 2 | 3 | 3 | 2.67 |
| Group 4 | 3 | 4 | 5 | 3 | 4 | 5 | 4.00 |
| Group 5 | 5 | 6 | 6 | 3 | 3 | 2 | 4.17 |
| Group 6 | 1 | 2 | 1 | 0 | 1 | 1 | 1.00 |
| Group 7 | 1 | 1 | 0 | 1 | 2 | 2 | 1.17 |

TABLE 7

Pole climbing test (time (sec))

| Groups | 1 | 2 | 3 | 4 | 5 | 6 | Average |
|---|---|---|---|---|---|---|---|
| Group 1 | 74 | 70 | 71 | 72 | 75 | 72 | 72.33 |
| Group 2 | 91 | 88 | 94 | 92 | 95 | 89 | 91.50 |
| Group 3 | 75 | 72 | 65 | 61 | 77 | 69 | 69.83 |
| Group 4 | 68 | 65 | 55 | 53 | 50 | 58 | 58.17 |
| Group 5 | 65 | 60 | 62 | 56 | 54 | 57 | 59.00 |
| Group 6 | 43 | 44 | 42 | 45 | 40 | 41 | 42.50 |
| Group 7 | 42 | 43 | 42 | 45 | 42 | 40 | 42.33 |

TABLE 8

Tau Protein-in Serum (ng/mL)

| Groups | 1 | 2 | 3 | 4 | 5 | 6 | Average |
|---|---|---|---|---|---|---|---|
| Group 1 | 0.35 | 0.33 | 0.34 | 0.37 | 0.40 | 0.38 | 0.36 |
| Group 2 | 1.25 | 1.20 | 1.60 | 1.35 | 1.50 | 1.38 | 1.38 |
| Group 3 | 1.20 | 1.00 | 1.40 | 1.15 | 1.30 | 1.15 | 1.20 |
| Group 4 | 1.10 | 0.80 | 0.90 | 0.80 | 1.00 | 1.10 | 0.95 |
| Group 5 | 1.10 | 1.00 | 0.90 | 1.00 | 0.80 | 1.00 | 0.97 |
| Group 6 | 0.48 | 0.50 | 0.47 | 0.32 | 0.44 | 0.38 | 0.43 |
| Group 7 | 0.50 | 0.33 | 0.47 | 0.47 | 0.48 | 0.37 | 0.44 |

TABLE 9

BDNF-in Serum (ng/mL)

| Groups | Animals | | | | | | |
|---|---|---|---|---|---|---|---|
| | 1 | 2 | 3 | 4 | 5 | 6 | Average |
| Group 1 | 30.00 | 28.90 | 32.00 | 30.20 | 30.00 | 29.70 | 30.13 |
| Group 2 | 16.10 | 15.50 | 18.90 | 16.00 | 17.40 | 14.80 | 16.45 |
| Group 3 | 18.10 | 19.00 | 21.50 | 20.00 | 22.00 | 18.50 | 19.85 |
| Group 4 | 21.00 | 21.10 | 23.50 | 20.20 | 21.20 | 23.80 | 21.80 |
| Group 5 | 22.00 | 22.50 | 22.30 | 21.00 | 23.00 | 22.60 | 22.23 |
| Group 6 | 31.00 | 32.00 | 31.40 | 31.60 | 32.00 | 32.10 | 31.68 |
| Group 7 | 30.30 | 30.10 | 31.00 | 31.40 | 29.00 | 29.50 | 30.22 |

TABLE 10

TNF-alfa (ng/mL)

| Groups | Animals | | | | | | |
|---|---|---|---|---|---|---|---|
| | 1 | 2 | 3 | 4 | 5 | 6 | Average |
| Group 1 | 1.80 | 2.00 | 1.00 | 1.20 | 1.40 | 1.30 | 1.45 |
| Group 2 | 3.20 | 4.00 | 3.70 | 4.20 | 3.80 | 3.50 | 3.73 |
| Group 3 | 3.00 | 3.50 | 3.20 | 3.80 | 3.10 | 3.30 | 3.32 |
| Group 4 | 2.80 | 2.60 | 2.90 | 2.80 | 2.90 | 2.70 | 2.78 |
| Group 5 | 2.80 | 3.10 | 2.50 | 3.00 | 2.60 | 3.00 | 2.83 |
| Group 6 | 1.20 | 1.30 | 1.34 | 1.50 | 1.60 | 1.45 | 1.40 |
| Group 7 | 1.35 | 1.40 | 1.34 | 1.52 | 1.70 | 1.30 | 1.44 |

TABLE 11

IL-6 (pg/ml) in cerebral cortex

| Groups | Animals | | | | | | |
|---|---|---|---|---|---|---|---|
| | 1 | 2 | 3 | 4 | 5 | 6 | Average |
| Group 1 | 30.3 | 28.2 | 26.9 | 25.4 | 26.9 | 28.2 | 27.65 |
| Group 2 | 44.70 | 43.80 | 45.90 | 46.10 | 49.00 | 47.80 | 46.22 |
| Group 3 | 34.30 | 30.20 | 33.40 | 35.30 | 33.50 | 35.00 | 33.62 |
| Group 4 | 36.40 | 36.70 | 37.00 | 36.80 | 36.50 | 36.70 | 36.68 |
| Group 5 | 37.80 | 36.50 | 35.70 | 34.80 | 36.50 | 36.80 | 36.35 |
| Group 6 | 21.70 | 24.80 | 24.70 | 23.80 | 24.20 | 22.40 | 23.60 |
| Group 7 | 25.00 | 26.00 | 23.20 | 22.60 | 21.50 | 22.80 | 23.52 |

TABLE 12

Ach (pg/mg)

| Groups | Animals | | | | | | |
|---|---|---|---|---|---|---|---|
| | 1 | 2 | 3 | 4 | 5 | 6 | Average |
| Group 1 | 71.05 | 82.50 | 83.60 | 78.05 | 76.50 | 83.50 | 79.20 |
| Group 2 | 52.40 | 48.05 | 44.05 | 52.20 | 51.50 | 53.50 | 50.28 |
| Group 3 | 63.20 | 64.80 | 66.50 | 62.50 | 67.20 | 65.50 | 64.95 |
| Group 4 | 68.00 | 69.50 | 70.00 | 68.00 | 67.00 | 68.20 | 68.45 |
| Group 5 | 67.00 | 68.50 | 68.80 | 68.00 | 67.90 | 68.20 | 68.07 |
| Group 6 | 89.00 | 89.00 | 92.00 | 91.20 | 88.90 | 91.70 | 90.30 |
| Group 7 | 91.50 | 89.80 | 92.40 | 91.80 | 93.00 | 94.00 | 92.08 |

The present investigation demonstrated the neuroprotective activity of test substances against memory deficits (cognitive impairment) in Swiss albino mice. It did not show any significant changes in Body weight in all the groups observed when compared with disease control group (G2) (Table 2).

Table 3 represents the feed intake of mice which did not show any significant changes observed in all the groups when compared with disease control group (G2).

Figure 1:
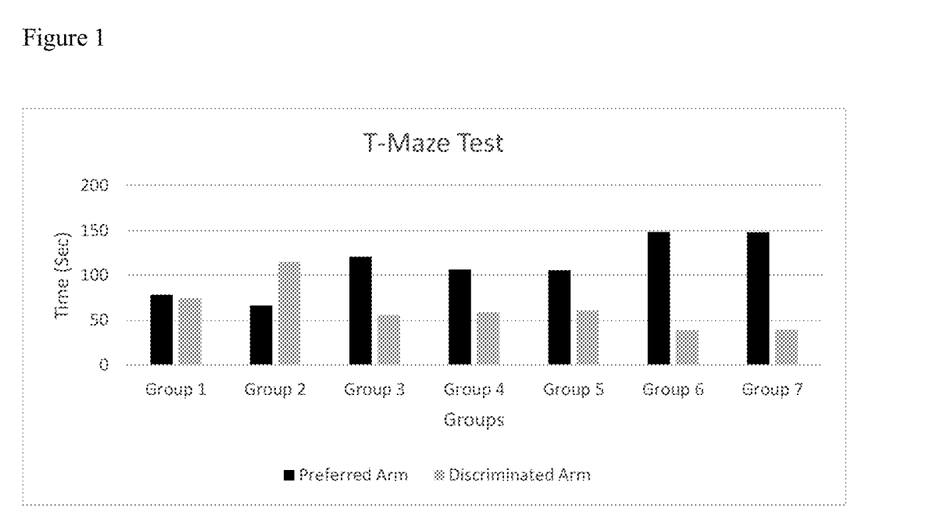
FIG. 1 illustrates time spent in preferred and discriminated arm in seconds (T-maze test)

Table 4 and FIG. 1 represent the time spent (sec) in the preferred and discriminated arm and showed significant increase in the G6 and G7 treated group when compared with Control group (G2) in preferred arm.

Figure 2:
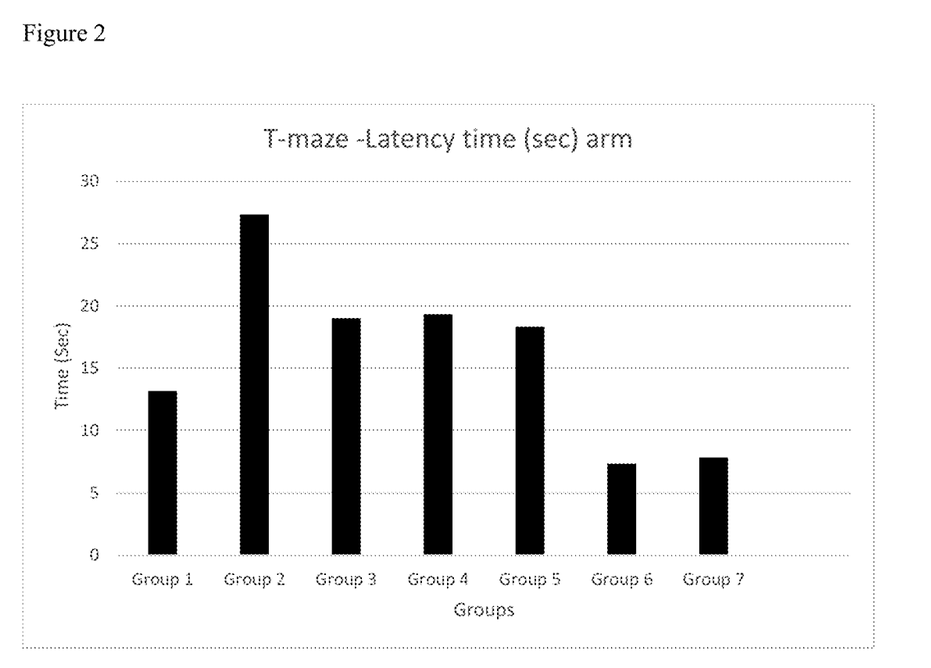
FIG. 2 illustrates latency time in seconds (T-maze test)

Table 5 and FIG. 2 represent the latency time (sec) in the preferred arm and showed significant decrease in G6 and G7 treated group when compared with Control group (G2) in preferred arm.

Figure 3:
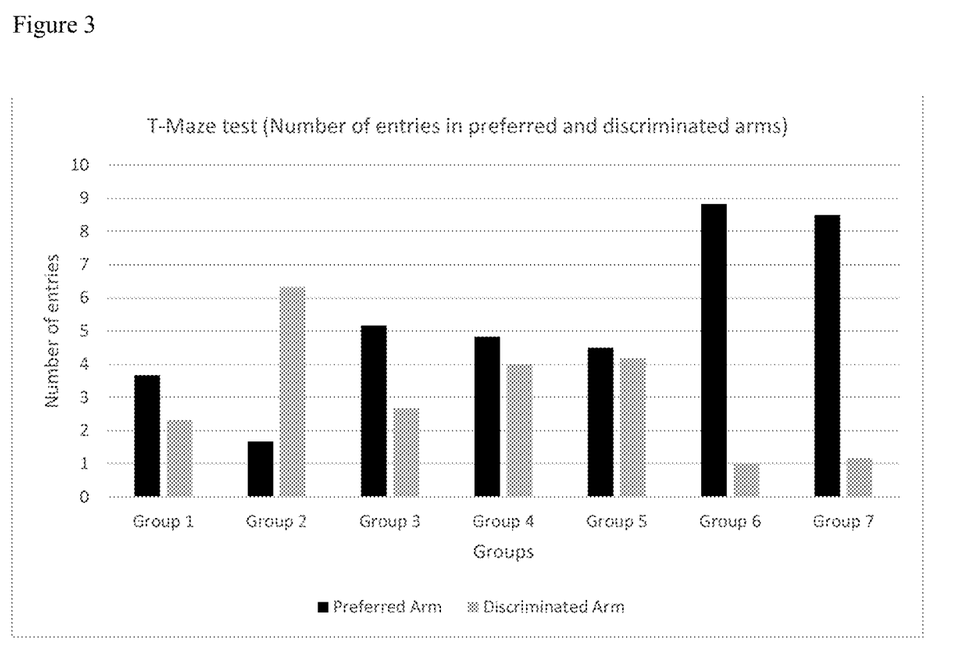
FIG. 3 illustrates number of entries in preferred and discriminated arm (T-maze test)

Table 6 and FIG. 3 represent the number of entries in preferred arm and showed significant improvement in G6 and G7 treated group when compared with Control group (G2) in preferred arm.

Figure 4:
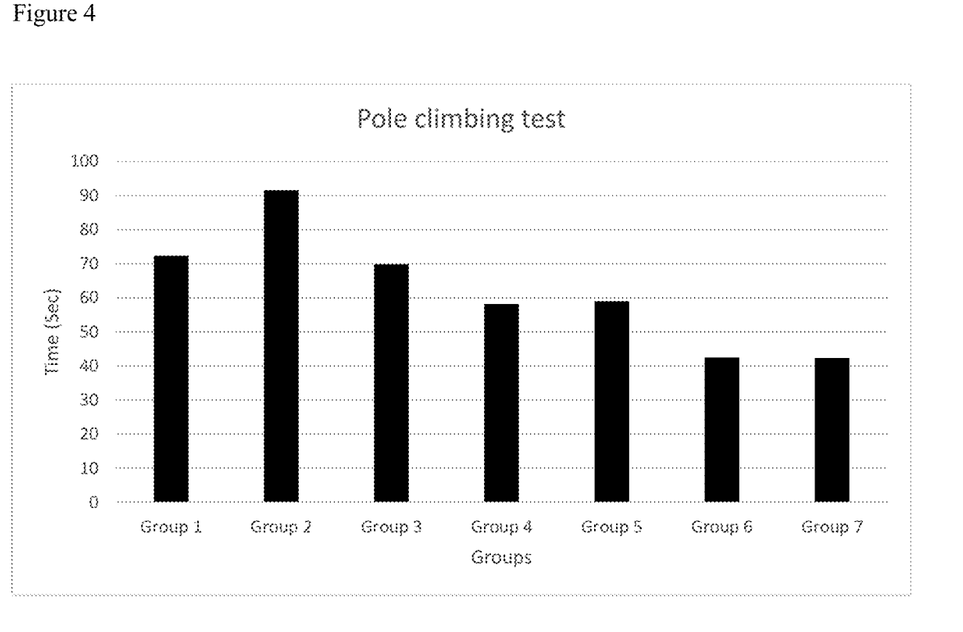
FIG. 4 illustrates pole climbing test in seconds

Table 7 and FIG. 4 represent the Pole climbing test (sec) which showed quick response in G6 and G7 treated group when compared with Control group (G2) in preferred arm.

Figure 5:
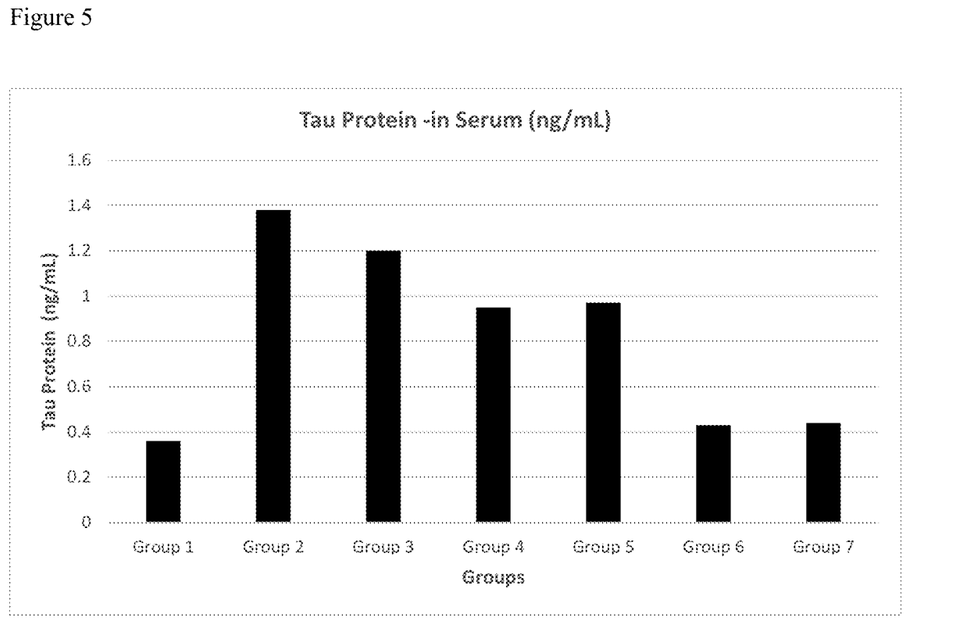
FIG. 5 illustrates tau protein in serum (ng/ml)
Figure 7:
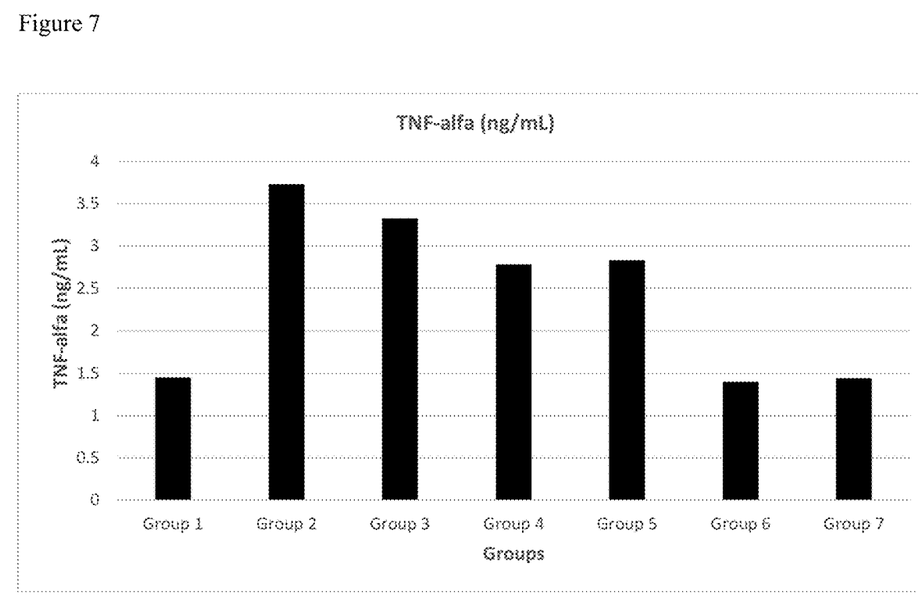
FIG. 7 illustrates TNF-α in serum (ng/ml)
Figure 8:
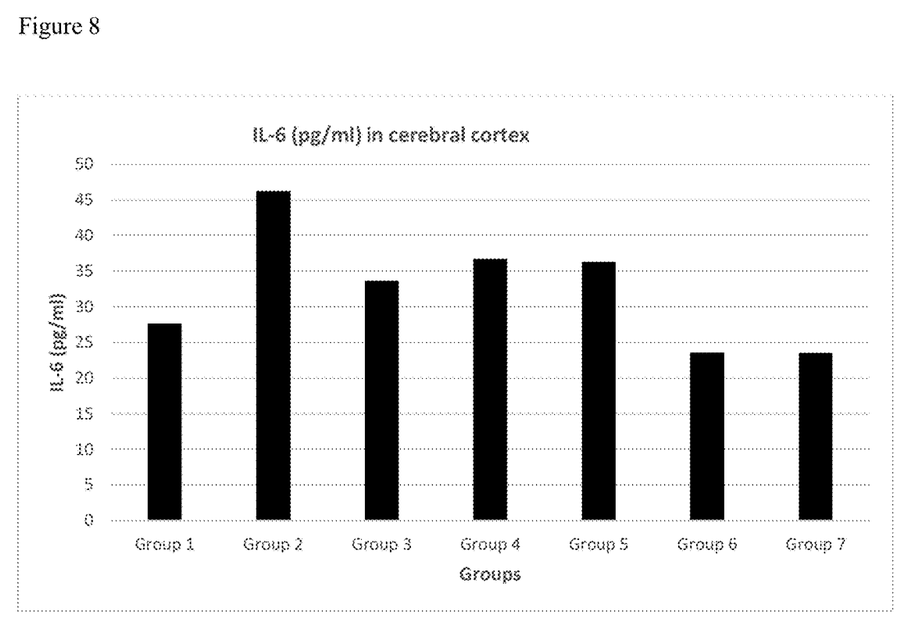
FIG. 8 illustrates IL-6 in cerebral cortex (pg/ml)

Tables 8, 10, 11 and FIGS. 5, 7, 8 respectively represent significant decrease in tau protein, TNF-α and IL-6 in G6 and G7 treated group when compared with Control group (G2).

Figure 6:
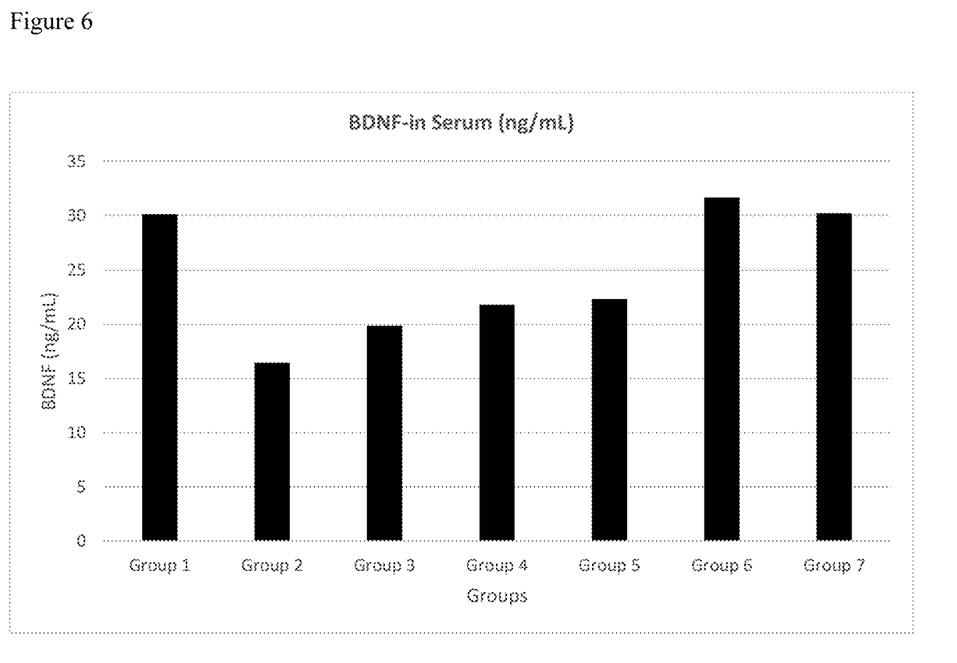
FIG. 6 illustrates BDNF in serum (ng/ml)
Figure 9:
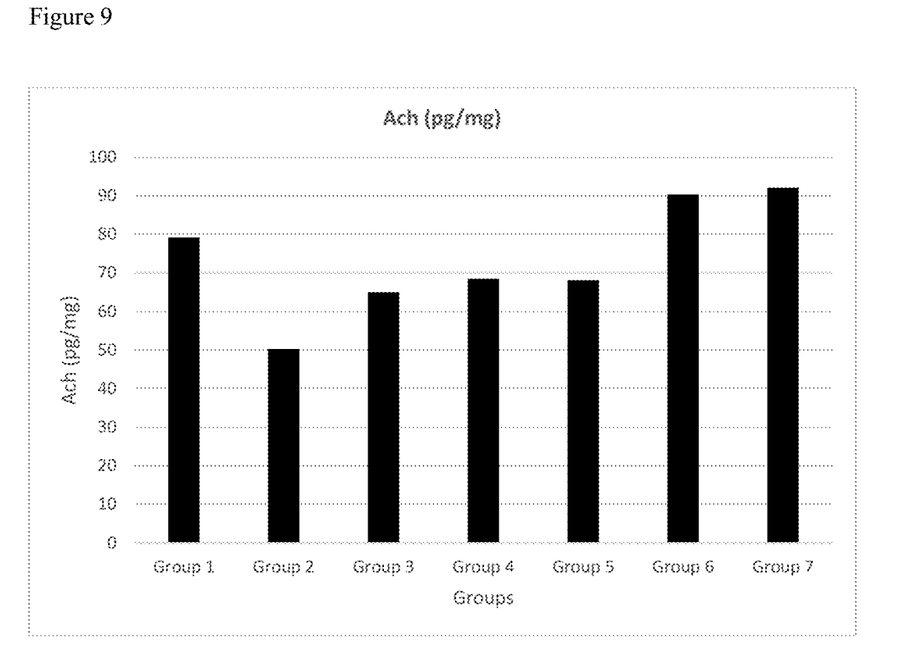
FIG. 9 illustrates Ach level (pg/ml)

Tables 9, 12 and FIGS. 6, 9 represent the significant increase in BDNF and Ach in G6 and G7 treated group when compared with Control group (G2).

CONCLUSION

The results showed that the combination of MgLT+ HT increases BDNF and Acetylcholine and reduces relative inflammation in brain and tau protein accumulation and rescue neurocognitive effectively.

It is concluded that, the combination of MgLT+ HT effectively prevents neuron cells from death caused by cytokines and reduces accumulation of hyperphosphorylated tau protein and progressive neuronal loss. The present combination effectively enhances synaptic density or plasticity through stimulation of BDNF. Further supplementing with present nutrient composition significantly improved memory and learning ability.

We claim:

1. A nutritional composition for treating neurocognitive disorder, the nutritional composition comprising:
    an exogenous blend; and
    pharmaceutically acceptable excipients,
    wherein the exogenous blend consists of magnesium L-threonate in a range of 50 to 250 mg and homotaurine in a range of 25 to 50 mg.

2. The nutritional composition according to claim 1, wherein the magnesium L-threonate and the homotaurine are present in a white crystalline form.

3. The nutritional composition according to claim 1, wherein the pharmaceutically acceptable excipients are selected from the group consisting of a diluent present in a range of 1 to 30%; a binder present in a range of 0.1 to 25%; a lubricant present in a range of 0.1 to 10.0%; a glidant present in a range of 0.1 to 5.0%; an additive present in a range of 1 to 10%; a surfactant present in a range of 0.1 to 5.0%; a stabilizer present in a range of 0.1 to 5.0%, an antioxidant present in a range of 0.1 to 5.0%; and a plasticizer present in a range of 0.1 to 5.0%, by weight of the total composition.

4. The nutritional composition according to claim 1, wherein the nutritional composition is administered orally to a subject.

* * * * *